(12) United States Patent
Lee et al.

(10) Patent No.: US 12,050,490 B2
(45) Date of Patent: Jul. 30, 2024

(54) STRETCHABLE DEVICE, DISPLAY PANEL, SENSOR, AND ELECTRONIC DEVICE

(71) Applicant: Samsung Electronics Co., Ltd., Suwon-si (KR)

(72) Inventors: Yeongjun Lee, Seongnam-si (KR); Youngjun Yun, Seongnam-si (KR); Jong Won Chung, Hwaseong-si (KR); Hyun Bum Kang, Yongin-si (KR); Gae Hwang Lee, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 428 days.

(21) Appl. No.: 17/542,988

(22) Filed: Dec. 6, 2021

(65) Prior Publication Data
US 2022/0334616 A1 Oct. 20, 2022

(30) Foreign Application Priority Data
Apr. 15, 2021 (KR) .................... 10-2021-0049241

(51) Int. Cl.
*G06F 1/00* (2006.01)
*A61B 5/00* (2006.01)
*G06F 1/16* (2006.01)
*G06F 1/18* (2006.01)
*H05K 1/02* (2006.01)
*H10K 77/10* (2023.01)

(52) U.S. Cl.
CPC .......... *G06F 1/1652* (2013.01); *A61B 5/6824* (2013.01); *A61B 5/6825* (2013.01); *G06F 1/189* (2013.01); *A61B 5/6833* (2013.01); *A61B 2562/164* (2013.01); *H05K 1/0283* (2013.01); *H10K 77/111* (2023.02)

(58) Field of Classification Search
CPC ..... G06F 1/1652; G06F 1/189; A61B 5/6824; A61B 5/6825; A61B 5/6833; A61B 2562/164; H10K 77/111; H05K 1/0283
See application file for complete search history.

(56) References Cited

U.S. PATENT DOCUMENTS

| 6,410,129 B2 | 6/2002 | Zhang et al. |
| 6,617,016 B2 | 9/2003 | Zhang et al. |
| 9,967,973 B2 | 5/2018 | Kim et al. |
| 10,090,479 B2 | 10/2018 | Kim et al. |
| 10,670,655 B2 | 6/2020 | Kim et al. |

(Continued)

FOREIGN PATENT DOCUMENTS

| JP | 4772244 B2 | 9/2011 |
| JP | 6656865 B2 | 3/2020 |

(Continued)

*Primary Examiner* — Pete T Lee
(74) *Attorney, Agent, or Firm* — Harness, Dickey & Pierce, P.L.C.

(57) ABSTRACT

A stretchable device includes a stretchable substrate having a plurality of incision lines that are configured to be deformable by an external force applied to the stretchable substrate, a plurality of active elements on the stretchable substrate, and a connection wire configured to electrically connect adjacent active elements of the plurality of active elements, wherein the connection wire includes a metal wire and a conductive elastic structure electrically connected to the metal wire and locally disposed in the connection wire.

20 Claims, 8 Drawing Sheets

(56) References Cited

U.S. PATENT DOCUMENTS

| | | | |
|---|---|---|---|
| 2002/0001707 A1 | 1/2002 | Zhang et al. | |
| 2002/0119301 A1 | 8/2002 | Zhang et al. | |
| 2013/0316487 A1* | 11/2013 | de Graff | A61B 1/04 438/66 |
| 2015/0282294 A1* | 10/2015 | Wakuda | H05K 1/118 29/850 |
| 2015/0351221 A1 | 12/2015 | Kim et al. | |
| 2016/0270700 A1* | 9/2016 | Baxi | A61B 5/6802 |
| 2018/0246165 A1 | 8/2018 | Kim et al. | |
| 2019/0116658 A1 | 4/2019 | Jeong et al. | |
| 2019/0232598 A1 | 8/2019 | Abbasi et al. | |
| 2021/0296554 A1 | 9/2021 | Ko et al. | |

FOREIGN PATENT DOCUMENTS

| | | |
|---|---|---|
| JP | 2020-072155 A | 5/2020 |
| KR | 10-1613588 B1 | 4/2016 |
| KR | 10-1960649 B1 | 3/2019 |
| KR | 2019-0042838 A | 4/2019 |
| KR | 10-2005060 B1 | 7/2019 |
| KR | 10-2044152 B1 | 11/2019 |
| KR | 10-2128237 B1 | 7/2020 |
| KR | 10-2152642 B1 | 9/2020 |

\* cited by examiner

STRETCHABLE DEVICE, DISPLAY PANEL, SENSOR, AND ELECTRONIC DEVICE

CROSS-REFERENCE TO RELATED APPLICATION

This application claims priority to and the benefit of, under 35 U.S.C. § 119, Korean Patent Application No. 10-2021-0049241 filed in the Korean Intellectual Property Office on Apr. 15, 2021, the entire contents of which are incorporated herein by reference.

BACKGROUND

1. Field

A stretchable device, a display panel, a sensor, and an electronic device are disclosed.

2. Description of the Related Art

Recently, research has been conducted on attachable devices that directly attach biological devices such as display devices or smart skin devices, soft robots, and biomedical devices to objects, skin, or clothes. Such an attachable device may be flexibly stretched according to the shape of an object or the movement of a living body and may have stretchability such that the attachable device may be restored to its original state after being stretched.

SUMMARY

Some example embodiments provide a stretchable device capable of improving stretching stability.

Some example embodiments provide a display panel including the stretchable device.

Some example embodiments provide a sensor including the stretchable device.

Some example embodiments provide an electronic device including the stretchable device, the display panel, or the sensor.

According to some example embodiments, a stretchable device includes a stretchable substrate having a plurality of incision lines that are configured to be deformable by an external force applied to the stretchable substrate, a plurality of active elements on the stretchable substrate, and a connection wire configured to electrically connect adjacent active elements of the plurality of active elements, wherein the connection wire includes a metal wire and a conductive elastic structure electrically connected to the metal wire and in a particular, limited portion of the connection wire.

The stretchable substrate may include a plurality of island-shaped regions, the plurality of active elements being on separate, respective island-shaped regions of the plurality of island-shaped regions. The stretchable substrate may include a stretchable region excluding the plurality of island-shaped regions. The plurality of incision lines may be in the stretchable region.

The connection wire may be disposed on the stretchable region of the stretchable substrate.

The conductive elastic structure may be in contact with a portion of the metal wire that is configured concentrate stress in the metal wire based on deformation of at least the stretchable substrate.

The conductive elastic structure may be in contact with an edge portion of the metal wire, a center portion of the metal wire, or any combination thereof.

The conductive elastic structure may be on a particular portion of the metal wire, or at least a portion of the conductive elastic structure may be embedded in the metal wire.

The conductive elastic structure may include a combination of an elastic polymer and at least one of a metal, a liquid metal, or a conductive nanostructure.

The conductive elastic structure may include an elastic layer including an elastic polymer, and a conductive layer on the elastic layer and including a metal, wherein the elastic layer may include a first depth region and a second depth region sequentially in a depth direction from a surface that is in contact with the conductive layer, and the first depth region may include the metal.

The elastic polymer may be a copolymer including at least one rigid structural unit and at least one soft structural unit, and a weight ratio of the rigid structural unit to the soft structural unit may be less than about 1 (e.g., greater than about 0.01 and less than about 1).

The rigid structural unit may include a styrene structural unit, an olefin structural unit, a urethane structural unit, an ether structural unit or any combination thereof, and the soft structural unit may include an ethylene structural unit, a propylene structural unit, a butylene structural unit, an isobutylene structural unit, a butadiene structural unit, an isoprene structural unit, or any combination thereof.

The metal may include gold (Au), silver (Ag), copper (Cu), rhodium (Rh), palladium (Pd), ruthenium (Ru), osmium (Os), iridium (Ir), platinum (Pt), an alloy thereof, or any combination thereof.

The metal in the first depth region of the elastic layer may exist in a form of a metal cluster.

The conductive layer may be electrically connected to the metal cluster of the elastic layer.

The metal cluster or the conductive layer of the elastic layer may be electrically connected to the metal wire.

The conductive layer may include a plurality of microcracks.

Each active element of the plurality of active elements may include a transistor, a light emitting element, a light absorption element, a resistive element, an imaging element, or any combination thereof.

According to some example embodiments, a display panel including the stretchable device is provided.

According to some example embodiments, a sensor including the stretchable device is provided.

According to some example embodiments, an electronic device including the stretchable device, the display panel, or the sensor is provided.

Stretching stability may be improved.

DETAILED DESCRIPTION

Figure 1:
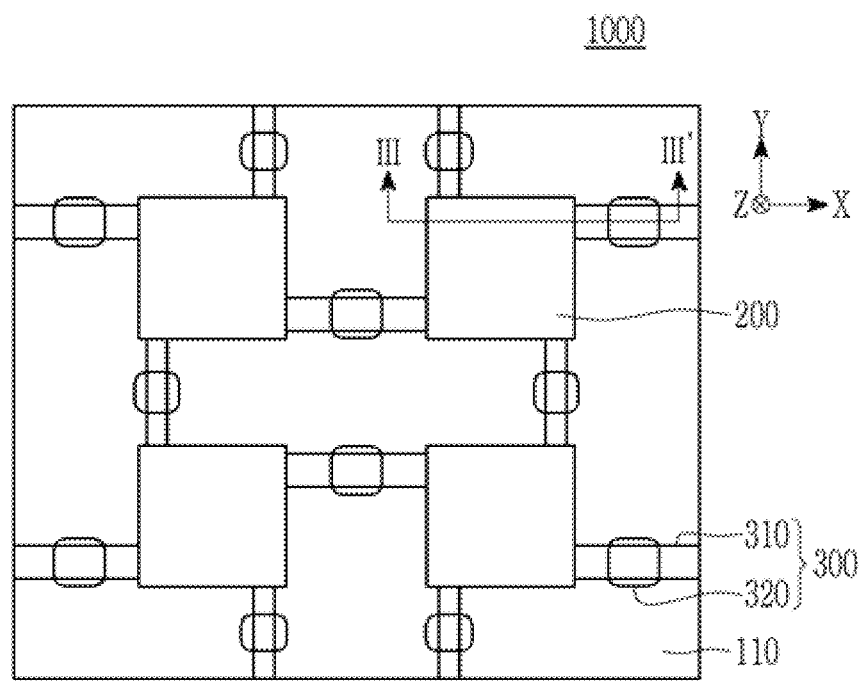
FIG. 1 is a plan view showing an example of a stretchable device according to some example embodiments.

Hereinafter, some example embodiments are described in detail so that those skilled in the art can easily implement them. However, the actual applied structure may be implemented in various different forms and is not limited to the example embodiments described herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, when a definition is not otherwise provided, "substituted" refers to replacement of hydrogen of a compound by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a silyl group, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

Hereinafter, the term "combination" includes a mixture, a composite, or a stacked structure of two or more.

Hereinafter, a stretchable device according to some example embodiments is described with reference to the drawings.

It will be understood that when an element such as a layer, film, region, or substrate is referred to as being "on" another element, it may be directly on the other element or intervening elements may also be present. In contrast, when an element is referred to as being "directly on" another element, there are no intervening elements present. It will further be understood that when an element is referred to as being "on" another element, it may be above or beneath or adjacent (e.g., horizontally adjacent) to the other element.

It will be understood that elements and/or properties thereof (e.g., structures, surfaces, directions, or the like), which may be referred to as being "perpendicular," "parallel," "coplanar," or the like with regard to other elements and/or properties thereof (e.g., structures, surfaces, directions, or the like) may be "perpendicular," "parallel," "coplanar," or the like or may be "substantially perpendicular," "substantially parallel," "substantially coplanar," respectively, with regard to the other elements and/or properties thereof.

Elements and/or properties thereof (e.g., structures, surfaces, directions, or the like) that are "substantially perpendicular" with regard to other elements and/or properties thereof will be understood to be "perpendicular" with regard to the other elements and/or properties thereof within manufacturing tolerances and/or material tolerances and/or have a deviation in magnitude and/or angle from "perpendicular," or the like with regard to the other elements and/or properties thereof that is equal to or less than 10% (e.g., a. tolerance of ±10%).

Elements and/or properties thereof (e.g., structures, surfaces, directions, or the like) that are "substantially parallel" with regard to other elements and/or properties thereof will be understood to be "parallel" with regard to the other elements and/or properties thereof within manufacturing tolerances and/or material tolerances and/or have a deviation in magnitude and/or angle from "parallel," or the like with regard to the other elements and/or properties thereof that is equal to or less than 10% (e.g., a. tolerance of ±10%).

Elements and/or properties thereof (e.g., structures, surfaces, directions, or the like) that are "substantially coplanar" with regard to other elements and/or properties thereof will be understood to be "coplanar" with regard to the other elements and/or properties thereof within manufacturing tolerances and/or material tolerances and/or have a deviation in magnitude and/or angle from "coplanar," or the like with regard to the other elements and/or properties thereof that is equal to or less than 10% (e.g., a. tolerance of ±10%)).

It will be understood that elements and/or properties thereof may be recited herein as being "the same" or "equal" as other elements, and it will be further understood that elements and/or properties thereof recited herein as being "identical" to, "the same" as, or "equal" to other elements may be "identical" to, "the same" as, or "equal" to or "substantially identical" to, "substantially the same" as or "substantially equal" to the other elements and/or properties thereof. Elements and/or properties thereof that are "substantially identical" to, "substantially the same" as or "substantially equal" to other elements and/or properties thereof will be understood to include elements and/or properties thereof that are identical to, the same as, or equal to the other elements and/or properties thereof within manufacturing tolerances and/or material tolerances. Elements and/or properties thereof that are identical or substantially identical to and/or the same or substantially the same as other elements and/or properties thereof may be structurally the same or substantially the same, functionally the same or substantially the same, and/or compositionally the same or substantially the same.

It will be understood that elements and/or properties thereof described herein as being "substantially" the same and/or identical encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

Figure 2:
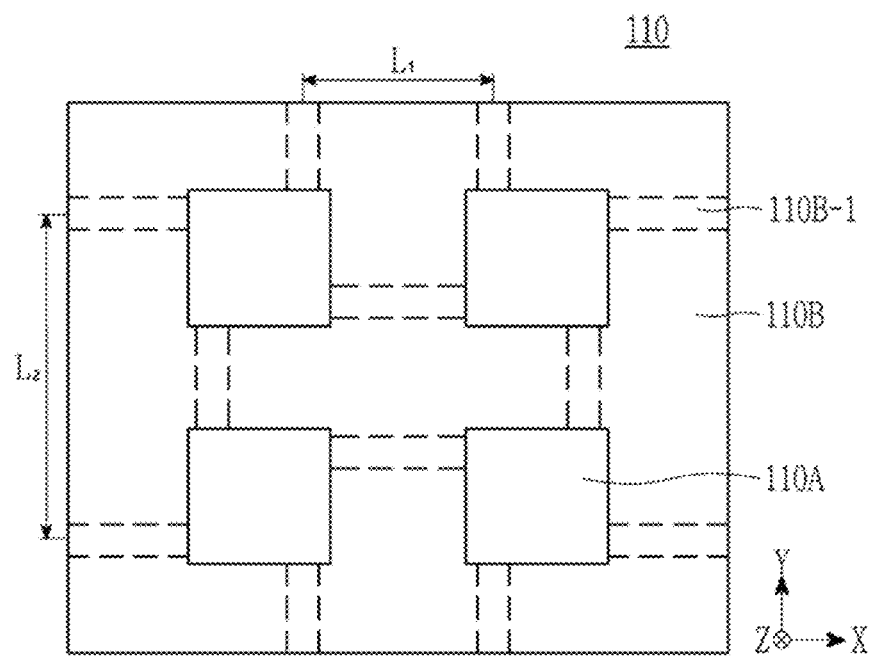
FIG. 2 is a plan view showing an example of the substrate in the stretchable device of FIG. 1 according to some example embodiments.
Figure 3:
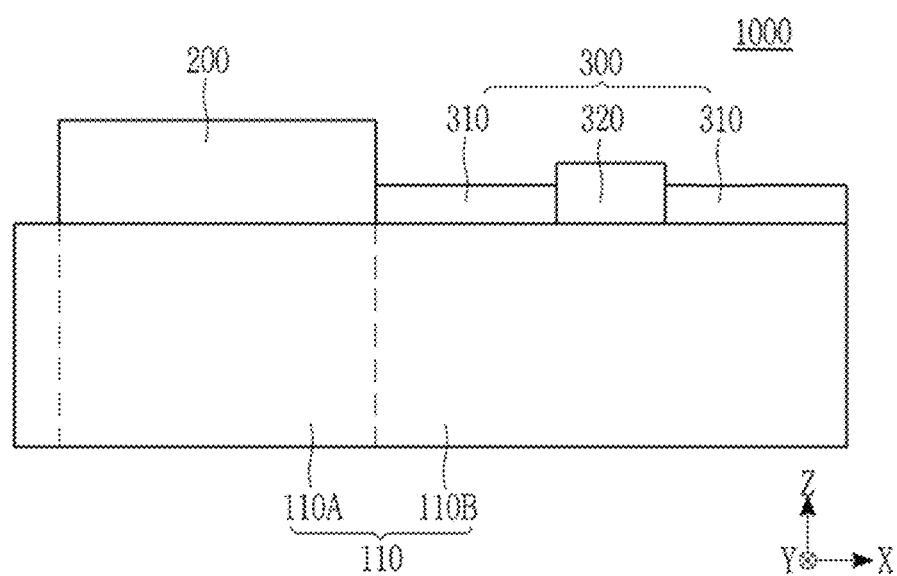
FIG. 3 is a cross-sectional view taken along the line III-III' of the stretchable device of FIG. 1 according to some example embodiments.
Figure 4:
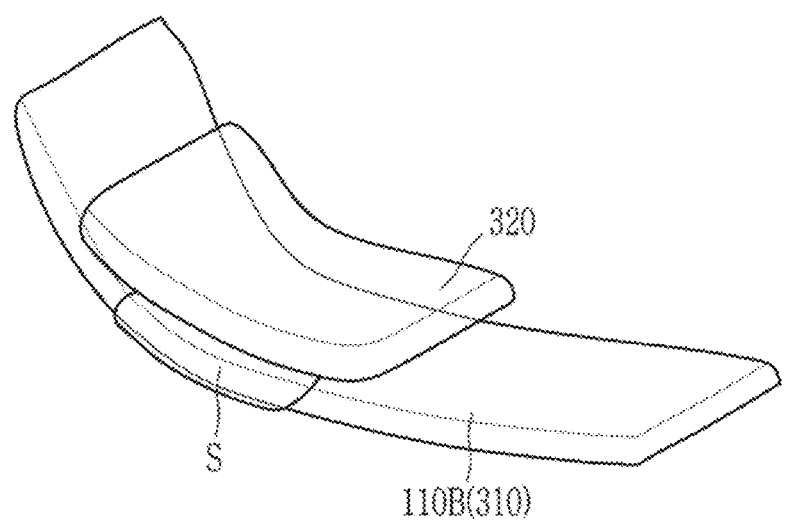
FIG. 4 is a schematic view showing an example of the local arrangement of the conductive elastic structure in the stretchable device of FIG. 1 according to some example embodiments.
Figure 5:
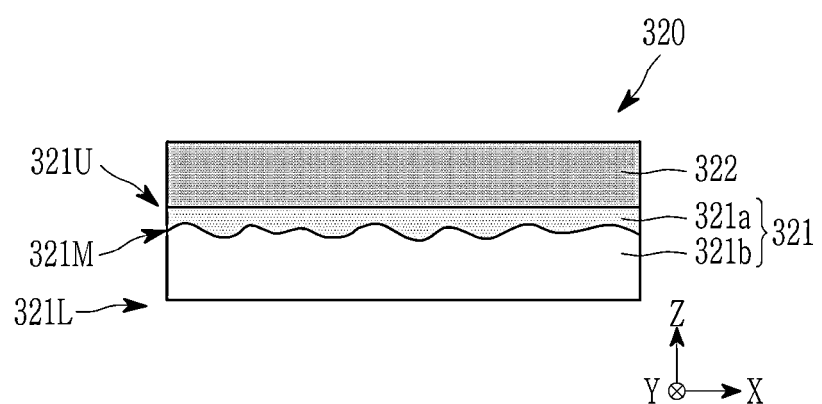
FIGS. 5 and 6 are cross-sectional views showing examples of a conductive elastic structure in the stretchable device of FIG. 1 according to some example embodiments.
Figure 6:
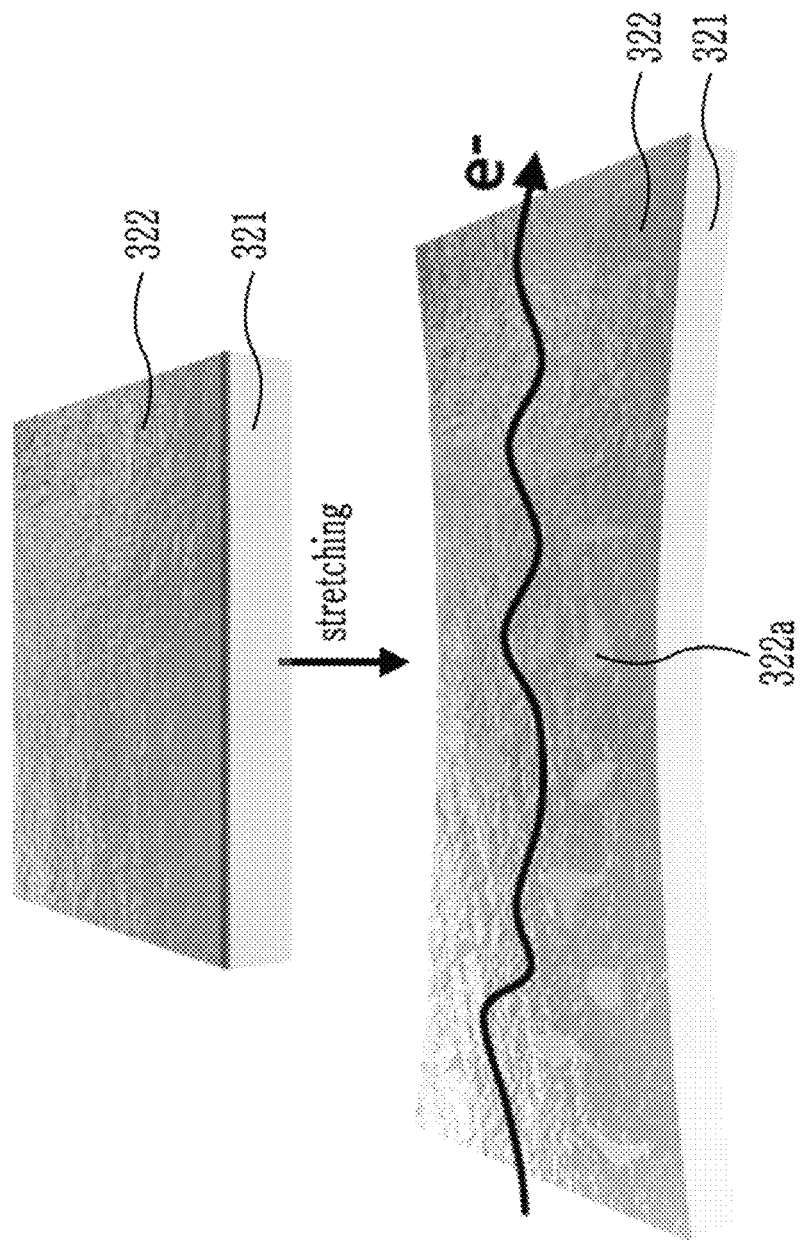

FIG. 1 is a plan view showing an example of a stretchable device according to some example embodiments, FIG. 2 is a plan view showing an example of the substrate in the stretchable device of FIG. 1 according to some example embodiments, FIG. 3 is a cross-sectional view taken along the line III-III' of the stretchable device of FIG. 1 according to some example embodiments, FIG. 4 is a schematic view showing an example of the local arrangement of the conductive elastic structure in the stretchable device of FIG. 1 according to some example embodiments, and FIGS. 5 and 6 are cross-sectional views showing examples of a conductive elastic structure in the stretchable device of FIG. 1 according to some example embodiments.

Referring to FIGS. 1 and 3, the stretchable device 1000 according to some example embodiments includes a substrate 110, a plurality of active elements 200 on the substrate 110, and a connection wire 300.

The substrate 110, as described herein, may be a stretchable substrate that may be stretchable in a particular (or, alternatively, predetermined) direction and may be restored again (e.g., may return to an original size and shape after being stretched). The stretchable substrate may flexibly respond to external forces or external movements such as twisting, pressing, and pulling in a particular (or, alternatively, predetermined) direction.

Hereinafter, a device, layer, element, region, or the like that is described as being "stretchable" will be understood to be elastic and/or configured to be elastic, such that the device, layer, element, region, or the like is configured to be elastically deformed (e.g., stretched, compressed, subjected to strain, etc.) such that the device, layer, element, region, or the like is configured to resume its same original shape after being deformed. For example, a stretchable device, layer, element, region, or the like as described herein may be capable of being elastically deformed such that the stretchable device, layer, element, region, or the like can resume, and does resume, an original shape after being stretched or compressed.

Hereinafter, a device, layer, element, region, or the like that is described as being "non-stretchable" will be understood to be non-elastic and/or not configured to be elastic, such that the device, layer, element, region, or the like is configured to not be elastically deformed (e.g., stretched, compressed, subjected to strain, etc.) such that the device, layer, element, region, or the like is configured to not resume its same original shape after being deformed. For example, a non-stretchable device, layer, element, region, or the like as described herein may not be able to be elastically deformed due to applied strain such that the non-stretchable device, layer, element, region, or the like cannot, and does not, resume an original shape after being stretched or compressed.

In some example embodiments, a stretchable device, layer, element, region, or the like may have an elastic modulus that is about $10^{-2}$ Pa to about $10^{10}$ Pa. In some example embodiments, a stretchable device, layer, element, region, or the like may have an elastic modulus that is greater than or equal to about $10^2$ Pa and less than about $10^8$ Pa.

The substrate 110, which may be a stretchable substrate, may include an elastic polymer having a particular (or, alternatively, predetermined) elastic modulus, where the elastic modulus may be, for example, Young's modulus. For example, the substrate 110 may be polycarbonate, polymethylmethacrylate, polyethyleneterephthalate, polyethylenenaphthalate, polyimide, polyamide, polyamideimide, polyethersulfone, a substituted or unsubstituted polyorganosiloxane such as polydimethylsiloxane, an elastomer including a substituted or unsubstituted butadiene moiety such as styrene-ethylene-butylene-styrene, an elastomer including a urethane moiety, an elastomer including acrylic moiety, an elastomer including an olefin moiety, or any combination thereof, but is not limited thereto.

For example, the substrate 110 may include an elastic polymer having a relatively high elastic modulus. For example, the elastic modulus of the substrate 110 may be, for example, about $10^5$ Pa to about $10^{12}$ Pa, about $10^6$ Pa to about $10^{12}$ Pa, or about $10^7$ Pa to about $10^{12}$ Pa, but is not limited thereto. For example, the substrate 110 may include polycarbonate, polymethyl methacrylate, polyethylene terephthalate, polyethylene naphthalate, polyimide, polyamide, polyamideimide, polyethersulfone, or any combination thereof, but is not limited thereto.

For example, the substrate 110 may include a combination of elastic polymers having different elastic modulus, and for example, may have a stacked structure of a soft layer having a relatively low elastic modulus and a rigid layer having a relatively high elastic modulus. For example, the soft layer may be a lower layer and the rigid layer may be an upper layer, and the rigid layer may be closer to the active element 200 to be described later than the soft layer.

For example, the soft layer may include a substituted or unsubstituted polyorganosiloxane such as polydimethylsiloxane, an elastomer including a substituted or unsubstituted butadiene moiety such as styrene-ethylene-butylene-styrene SEBS, an elastomer including a urethane moiety, an elastomer comprising an acrylic moiety, an elastomer including an olefin moiety, or any combination thereof, and the rigid layer may include polycarbonate, polymethyl methacrylate, polyethylene terephthalate, polyethylene naphthalate, polyimide, polyamide, polyamideimide, polyethersulfone, or any combination thereof.

Referring to FIG. 2, the substrate 110 includes a plurality of island-shaped regions 110A on which a plurality of active elements 200 to be described later are to be formed, and a stretchable region 110B excluding the plurality of island-shaped regions 110A. For example, referring to FIGS. 1-3, the plurality of active elements 200 may be on separate, respective island-shaped regions 110A of the plurality of island-shaped regions 110A. The stretchable region 110B includes a wire region 110B-1 on which a connection wire 300 to be described later is disposed. The plurality of island-shaped regions 110A may be spaced apart from each other at a particular (or, alternatively, predetermined) interval and may be arranged, for example, in an in-plane direction (e.g., XY direction) of the substrate 110. The stretchable region 110B is an entire region except for the island-shaped regions 110A, and may be connected over the entire substrate 110.

A plurality of incision lines (not shown) are formed in the stretchable region 110B of the substrate 110 and may be deformable by an external force. Accordingly, in some example embodiments, the substrate 110 may be a stretchable substrate that has a plurality of incision lines that are configured to be deformable by an external force acting on (e.g., applied to) the substrate 110. The incision lines may be geometrically deformable while being widened or twisted by stretching of the substrate 110, thereby providing effective stretchability to the substrate 110 having a relatively high elastic modulus. The shape, position, and/or size of the plurality of incision lines may be geometrically pre-calculated and determined in consideration of the stretching direction of the substrate 110, the arrangement of the active element 200, and the like. The plurality of incision lines may be repeatedly arranged along the in-plane direction (e.g., XY direction) of the substrate 110, and thus, when stretched in a particular (or, alternatively, predetermined) direction (e.g., X, Y, and/or XY direction), repeat geometrical deformation on the substrate 110 may occur. Such a structure may be called a so-called "kirigami structure", and the incision line and adjacent patterns (cut patterns) divided by the incision lines may be wider, stretched, or twisted, and accordingly, a separation gap between adjacent patterns (cut patterns) may be changed according to the presence or absence of stretching or the strength of stretching. For example, the separation gaps $L_1$ and $L_2$ between the adjacent wire regions 110B-1 may be changed according to the presence or absence of stretching or the strength of stretching. Due to the two-dimensional and/or three-dimensional structural deformation, stretching and restoration in the stretching direction may be easy, so that effective stretchability may be provided to the stretchable region 110B of the substrate 110.

Referring to FIGS. 1 and 3, the plurality of active elements 200 are disposed on the island-shaped region 110A of the substrate 110, and may be, for example, arranged along rows and/or columns of the substrate 110 to form an array. The plurality of active elements 200 may be arranged in, for example, a Bayer matrix, a PenTile matrix, and/or a diamond matrix, but is not limited thereto. The plurality of active elements 200 may be disposed on the island-shaped regions 110A of the substrate 110 which is relatively stable against external force, so that stretching stability may be increased.

The plurality of active elements 200 may be the same or different from each other, and each active element 200 may include, for example, a light emitting element such as an organic light emitting diode, an inorganic light emitting diode, a quantum dot light emitting diode, a micro light emitting diode, or a perovskite light emitting diode; a light absorption element such as a photoelectric conversion element; a transistor such as a thin film transistors; a resistance element (e.g., resistive element); an imaging element, or any combination thereof, but are not limited thereto. Each active element 200 may include a conductor such as an electrode, a semiconductor such as an active layer, and an insulator, but is not limited thereto.

For example, each active element 200 may be a light emitting element that independently displays red, green, blue, or any combination thereof. For example, the light emitting element may include a pair of electrodes, and a light emitting layer between the pair of electrodes and configured to emit light in a red wavelength spectrum, a green wavelength spectrum, a blue wavelength spectrum, an infrared wavelength spectrum, an ultraviolet wavelength spectrum, or any combination thereof.

For example, each active element 200 may be a light absorption element configured to absorb light in a red wavelength spectrum, a green wavelength spectrum, a blue wavelength spectrum, an infrared wavelength spectrum, an ultraviolet wavelength spectrum, or any combination thereof. For example, the light absorption element may include a pair of electrodes and a light absorbing layer between the pair of electrodes and configured to absorb light in a red wavelength spectrum, a green wavelength spectrum, a blue wavelength spectrum, an infrared wavelength spectrum, an ultraviolet wavelength spectrum, or any combination thereof.

For example, the plurality of active elements 200 may include a plurality of light emitting elements and a plurality of light absorption elements alternately arranged along rows and/or columns.

For example, each active element 200 may include one or more thin film transistors. The thin film transistor may include, for example, a switching transistor and/or a driving transistor. The switching transistor may be electrically connected to the gate line and the data line and may include a first gate electrode connected to the gate line; a first source electrode connected to the data line; a first drain electrode facing the first source electrode; and a first semiconductor which is respectively electrically connected to the first source electrode and the first drain electrode. The driving transistor may include a second gate electrode electrically connected to the first drain electrode; a second source electrode connected to the driving voltage line; a second drain electrode facing the second source electrode; and a second semiconductor which is respectively electrically connected to the second source electrode and the second drain electrode. For example, the first semiconductor and the second semiconductor may each include a semiconductor material and an elastomer. For example, the first semiconductor and the second semiconductor may each include an organic semiconductor material and an elastomer.

Although all the active elements 200 are illustrated as having the same size in the drawings, the present inventive concepts are not limited thereto, and one or more active elements 200 may be larger or smaller than the other active elements 200. In the drawings, all of the active elements 200 are illustrated as having the same shape, but the present inventive concepts are not limited thereto, and one or more active elements 200 may have different shapes from other active elements 200.

The connection wire 300 may be on the stretchable region 110B of the substrate 110 and may be between the adjacent active elements 200 of the plurality of active elements 200 to electrically connect the adjacent active elements 200.

The connection wire 300 includes a metal wire 310 and a conductive elastic structure 320.

The metal wire 310 may be an electrical wire extending between adjacent active elements 200 and may include, for example, a low-resistance conductor such as silver, gold, copper, aluminum, or an alloy thereof, but is not limited thereto. Each metal wire 310 may be one or more than one, and may be arranged along a row direction (e.g., X direction) and column direction (e.g., Y direction) between active elements 200 arranged along rows and/or columns. However, the present inventive concepts are not limited thereto and the metal wire 310 may be arranged obliquely at a particular (or, alternatively, predetermined) angle with respect to the row direction (e.g., the X direction) and the column direction (e.g., the Y direction). The metal wire 310 may be connected to a signal line (not shown), and the signal line may include, for example, a gate line configured to transmit a gate signal (or a scan signal), a data line configured to transmit a data signal, and a driving voltage line configured to apply a driving voltage, and/or a common voltage line configured to apply a common voltage, but is not limited thereto.

As shown in FIGS. 1 and 3, the conductive elastic structure 320 is electrically connected to the metal wire 310 and may be locally in (e.g., in and/or on a particular, limited portion of) the connection wire 300. Since the conductive elastic structure 320 has conductivity and a relatively low elastic modulus, stretchability may be improved while maintaining or supplementing the electrical characteristics of the connection wire 300.

For example, as shown in FIG. 3, at least a portion of the conductive elastic structure 320 may be embedded in the metal wire 310. However, the present inventive concepts are not limited thereto, and the conductive elastic structure 320 may be in contact with the metal wire 310 on the upper or lower portion of the metal wire 310. For example as shown in FIGS. 1 and 3 and as further shown in FIG. 4, the conductive elastic structure 320 may be locally on the metal wire 310 so as to be on (e.g., in direct contact with) a particular, limited portion of the metal wire.

As an example, referring to FIG. 4, the conductive elastic structure 320 may be in (e.g., may be in contact with) a portion S where stress is concentrated in the stretchable region 1108 of the substrate 110 and the metal wire 310 based on deformation of at least the substrate 110. The portion S may be a particular portion of the metal wire 310 and/or a particular portion of the stretchable region 1108. Thus, the conductive elastic structure 320 may be on a particular limited portion S of the metal wire 310 and thus may be understood to be locally on the metal wire 310 at the portion S thereof. The stress may be applied to the metal wire 310 by deformation such as compression, tension, bending, and/or twisting of the substrate 110, and the portion S where the stress is concentrated may be an area where deformation, such as compression, tension, bending, and/or twisting, is concentrated. The portion S may be understood to be a particular portion of the metal wire 310 and/or the stretchable region 1108 that is configured to concentrate stress applied to the metal wire 310 based on deformation of at least the substrate 110. The portion S where the stress is concentrated may be determined by various causes. For example, the stress may be concentrated on a portion of the metal wire 310 by geometrical deformation by the incision lines of the substrate 110 described above, and for example, the stress may be concentrated in an edge portion of the metal wire 310, a center portion of the metal wire 310, or any combination thereof of the metal wire 310, and such portions may be the portion S. The portion S where the stress is concentrated may have a relatively higher relative stress than that of the aforementioned substrate 110 or metal wire 310. For example, the stress may be greater than or equal to about 200%, greater than or equal to about 250%, greater than or equal to about 300%, within the above range, greater than or equal to about 500%, greater than or equal to about 750%, or greater than or equal to about 1000%, within the above range, about 200% to about 10000%, about 250% to about 10000%, about 300% to about 10000%, about 500% to about 10000%, or about 750% to about 10000%. Here, the relative stress may be a percentage with respect to the stress of the aforementioned substrate 110 or the metal wire 310. Accordingly, the conductive elastic structure 320 may be formed to be in contact with the edge portion, the center portion, or any combination thereof of the metal wire 310, and accordingly, the conductive elastic structure 320 may provide the connection wire 300 with stretchability in the portion S where the stress is concentrated and may prevent damage and/or short circuit of the connection wire 300.

The conductive elastic structure 320 may be a structure having both conductivity and elasticity. For example, the conductive elastic structure 320 may be electrically connected to the metal wire 310, and may have a lower elastic modulus than the metal wire 310.

For example, the conductive elastic structure 320 may include a combination of a conductor and an elastomer, for example, a combination of a conductor and an elastic polymer, and for example, a combination of at least one of a metal, a liquid metal, or a conductive nanostructure, and an elastic polymer. The conductive elastic structure 320 may include a combination of an elastic polymer and at least one of a metal, a liquid metal, or a conductive nanostructure. The conductive nanostructure may be, for example, a conductive nanowire, a conductive nanotube, a conductive nanofiber, a conductive nanoparticle, or any combination thereof, but is not limited thereto. The conductive elastic structure 320 may be, for example, a combination of a metal and an elastic polymer, a combination of a liquid metal and an elastic polymer, or a combination of a conductive nanostructure and an elastic polymer. The combination herein may include a mixture, a composite, and/or a stacked structure.

For example, referring to FIG. 5, the conductive elastic structure 320 may be a combination of a metal and an elastic polymer, and may include an elastic layer 321 including an elastic polymer and a conductive layer 322 including a metal.

The elastic layer 321 may have stretchability that it may be stretchable in a particular (or, alternatively, predetermined) direction and may be restored again, and may flexibly respond to external forces or external movements such as twisting, pressing, and pulling in a particular (or, alternatively, predetermined) direction. The elastic layer 321 may have a relatively low elastic modulus, and the elastic modulus of the elastic layer 321 may be, for example, greater than or equal to about $10^2$ Pa and less than about $10^8$ Pa, and within the above range, greater than or equal to about $10^2$ Pa and less than or equal to about $10^7$ Pa, greater than or equal to about $10^2$ Pa and less than or equal to about $10^6$ Pa, or greater than or equal to about $10^2$ Pa and less than or equal to about $10^5$ Pa.

The stretching rate of the elastic layer 321 may be greater than or equal to about 20%, within the above range, about 50% or more, about 100% or more, about 120% or more, greater than or equal to about 150%, greater than or equal to about 200%, greater than or equal to about 250%, or greater than or equal to about 300%, or, within the above range, about 20% to about 1000%, about 50% to about 1000%, about 100% to about 1000%, about 120% to about 1000%, about 150% to about 1000%, about 200% to about 1000%, about 250% to about 1000%, or about 300% to about 1000%. Here, the stretching rate may be a percentage of the length change increased to the breaking point with respect to the initial length.

The elastic layer 321 may include an elastic polymer having a relatively low elastic modulus. The elastic polymer may be, for example, a thermoplastic elastomer, a thermosetting elastomer, or any combination thereof, and may include a plurality of structural units that are the same or different from each other.

For example, the elastic polymer may be a thermoplastic elastic polymer including at least one rigid structural unit providing relatively rigid physical properties and at least one soft structural unit providing relatively soft physical properties. For example, the elastic polymer may be a copolymer including at least one rigid structural unit providing relatively rigid physical properties and at least one soft structural unit providing relatively soft physical properties. The rigid structural unit may provide plastic properties such as, for example, high-temperature performance, thermoplastic processability, tensile strength and tear strength and the soft structural unit may provide low-temperature performance, hardness, flexibility, and elastomeric properties such as tension/compression. The rigid structural units and the soft structural units may be respectively alternately arranged or arranged in clusters or blocks in the elastic polymer.

The rigid structural unit may include, for example, a styrene-containing structural unit (hereinafter referred to as a "styrene structural unit"), an olefin-containing structural unit (hereinafter referred to as an "olefin structural unit"), a urethane-containing structural unit (hereinafter referred to as a "urethane structural unit"), an ether-containing structural unit (hereinafter referred to as an "ether structural unit"), or any combination thereof, but is not limited thereto.

The soft structural unit may include, for example, an ethylene-containing structural unit (hereinafter referred to as an "ethylene structural unit"), a propylene-containing structural unit (hereinafter referred to as a "propylene structural unit"), a butylene-containing structural unit (hereinafter referred to as a "butylene structural unit"), an isobutylene-containing structural unit (hereinafter referred to as "isobutylene structural unit"), a butadiene-containing structural unit (hereinafter referred to as a "butadiene structural unit"), an isoprene-containing structural unit (hereinafter referred to as an "isoprene structural unit"), or any combination thereof, but is not limited thereto.

For example, the rigid structural unit may be a styrene structural unit, and the soft structural unit includes an ethylene structural unit, a propylene structural unit, a butylene structural unit, an isobutylene structural unit, a butadiene structural unit, an isoprene structural unit, or any combination thereof.

For example, the elastic polymer may include a styrene-butadiene rubber (SBR), styrene-ethylene-butylene-styrene (SEBS), styrene-ethylene-propylene-styrene (SEPS), styrene-butadiene-styrene (SBS), styrene-isoprene-styrene (SIS), styrene-isobutylene-styrene (SIBS), or any combination thereof.

The elastic polymer may have a relatively low glass transition temperature (Tg). Since the elastic layer 321 includes an elastic polymer having a relatively low glass transition temperature, in the process of thermally depositing a conductive layer 322 to be described later on the elastic layer 321, penetration and/or diffusion of metal into the surface and interior of the elastic layer 321 may be facilitated due to the increased flexibility and increased free volume of the elastic polymer chains in the elastic layer 321.

The glass transition temperature of the elastic polymer may be, for example, less than or equal to about 80° C., within the above range, less than or equal to about 75° C., less than or equal to about 70° C., less than or equal to about 65° C., or less than or equal to about 60° C., for example greater than or equal to about −80° C., greater than or equal to about −70° C., greater than or equal to about −60° C., greater than or equal to about 0° C., greater than or equal to about 5° C., greater than or equal to about 10° C., greater than or equal to about 20° C., greater than or equal to about 25° C., or greater than or equal to about 30° C., or within the above range, about −80° C. to about 80° C., about −80° C. to about 75° C., about −80° C. to about 70° C., about −60° C. to about 65° C., or about −30° C. to about 60° C.

As such, an elastic polymer having a relatively low glass transition temperature may be obtained by controlling the ratio of a structural unit having a relatively high glass transition temperature to a structural unit having a relatively low glass transition temperature. For example, the structural unit having a relatively high glass transition temperature may be selected from the aforementioned rigid structural units, and the structural unit having a relatively low glass transition temperature may be selected from the aforementioned soft structural units. For example, a weight ratio of the rigid structural unit to the soft structural unit of the elastic polymer may be less than about 1, and within the above range, less than or equal to about 0.9, less than or equal to about 0.8, less than or equal to about 0.7, less than or equal to about 0.6, less than or equal to about 0.5, less than or equal to about 0.4, or less than or equal to about 0.3, or about 0.01 to about 0.9, about 0.01 to about 0.8, about 0.01 to about 0.7, about 0.01 to about 0.6, about 0.01 to about 0.5, about 0.01 to about 0.4, or about 0.01 to about 0.3.

For example, the elastic polymer may be styrene-ethylene-butylene-styrene (SEBS) including a styrene structural unit as a rigid structural unit and an ethylene structural unit and a butylene structural unit as a soft structural unit. By controlling the weight ratio of the styrene structural unit to the ethylene structural unit and the butylene structural unit, an elastic polymer having a relatively low glass transition temperature of, for example, less than or equal to about 80° C. may be obtained. For example, in the styrene-ethylene-butylene-styrene (SEBS), the weight ratio of the styrene structural unit to the ethylene structural unit and the butylene structural unit may be may be less than about 1, and within the above range, less than or equal to about 0.9, less than or equal to about 0.8, less than or equal to about 0.7, less than or equal to about 0.6, less than or equal to about 0.5, less than or equal to about 0.4, or less than or equal to about 0.3, or about 0.01 to about 0.9, about 0.01 to about 0.8, about 0.01 to about 0.7, about 0.01 to about 0.6, about 0.01 to about 0.5, about 0.01 to about 0.4, or about 0.01 to about 0.3.

The elastic layer 321 may have a first depth region 321a and a second depth region 321b sequentially disposed along a depth direction (e.g., Z direction) from an upper surface 321U that is in contact (e.g., direct contact) with the conductive layer 322. The first depth region 321a may be a region from the upper surface 321U in contact with the conductive layer 322 to a particular (or, alternatively, predetermined) depth, and the second depth region 321b may be a region from the boundary 321M with the first depth region 321a to the lower surface 321L of the elastic layer 321. The first depth region 321a and the second depth region 321b may be determined depending on whether a metal to be described later is included, and the boundary 321M between the first depth region 321a and the second depth region 321b may be a boundary through which the metal penetrates and/or diffuses during thermal deposition of the metal in order to form the conductive layer 322 to be described later. The thickness of the first depth region 321a may not be constant depending on the location.

The first depth region 321a of the elastic layer 321 may include a metal. The metal included in the first depth region 321a of the elastic layer 321 may be derived from metal atoms that are penetrated or diffused into the inside through the upper surface 321U of the elastic layer 321 during thermal evaporation of the metal in order to form a conductive layer 322 to be described later. Accordingly, the type of metal included in the first depth region 321a of the elastic layer 321 may be the same as the type of metal included in the conductive layer 322.

The metal may be selected from metals with low reactivity. For example, the metal may be and/or may include an inert metal (noble metal), for example, gold (Au), silver (Ag), copper (Cu), rhodium (Rh), palladium (Pd), ruthenium (Ru), osmium (Os), iridium (Ir), platinum (Pt), an alloy thereof, or any combination thereof, but is not limited thereto.

For example, the metal atoms that are penetrated and/or diffused inside through the upper surface 321U of the elastic layer 321 may aggregate with each other to form metal clusters. Accordingly, at least a portion of the metal in the first depth region 321a of the elastic layer 321 may exist in the form of a metal cluster.

The first depth region 321a of the elastic layer 321 may have, for example, a thickness of about 2 nm to about 100 nm, within the above range, about 2 nm to about 70 nm, about 2 nm to about 50 nm, about 2 nm to about 40 nm, about 2 nm to about 30 nm, about 2 nm to about 25 nm, about 2 nm to about 20 nm, about 2 nm to about 15 nm, or about 2 nm to about 10 nm, but is not limited thereto.

The conductive layer 322 may be on the elastic layer 321 and may be a metal layer formed to a particular (or, alternatively, predetermined) thickness on the elastic layer 321. The conductive layer 322 may include the same type of metal as the metal included in the first depth region 321a of the aforementioned elastic layer 321. The conductive layer 322 may include, for example, an inert metal such as gold (Au), silver (Ag), copper (Cu), rhodium (Rh), palladium (Pd), ruthenium (Ru), osmium (Os), iridium (Ir), or platinum (Pt); an alloy thereof; or any combination thereof, but is not limited thereto.

The conductive layer 322 may be a thin film deposited by thermal evaporation as will be described later, and may be a fine pattern having a particular (or, alternatively, predetermined) width and length. For example, the conductive layer 322 may have an island shape, a linear shape, or a wavy shape, but is not limited thereto.

Referring to FIG. 6, the conductive layer 322 may have and/or may comprise a plurality of microcracks 322a, and the plurality of microcracks 322a may expand along the stretching direction during stretching to be increased in size. In general, microcracks are microscopic cracks in a material. Microcracks are small linear or non-linear cracks that take the form of planar ellipses, typically with dimensions of about 1 micrometer to hundreds of micrometers. It may occur on a coating during the application or drying process, or during load strain of a coating or material. With microcracking, a material's strength, stiffness and stability decrease, possibly leading to undesirable properties such as a failure to protect the underlying materials from environmental contact and corrosion. Microcracks may form before the strain on a material reaches its breakpoint. As such, strain on materials should be limited before the resin fibers start to break. For example, the plurality of microcracks 322a may be intentionally or unintentionally formed during the formation of the conductive layer 322 or the stretching of the conductive layer 322. The plurality of microcracks 322a may prevent or reduce cracking or breaking of the conductive layer 322 during stretching by imparting flexibility or stretchability to the conductive layer 322. In addition, since the microcracks 322a are separated from each other like small holes in the conductive layer 322, unlike general linear cracks, a current path in the conductive layer 322 during stretching may be continuously connected without being blocked by the microcracks 322a, and thus electrical stability may be secured without damage to an electrical path due to the stretching.

The conductive layer 322 may be electrically connected to a metal (e.g., a metal cluster) existing in the first depth region 321a of the aforementioned elastic layer 321. For example, the conductive layer 322 may be in contact with at least a portion of the metal present in the first depth region 321a of the elastic layer 321. Therefore, it is possible to increase the adherence between the conductive layer 322 and the upper surface 321U of the elastic layer 321, thereby preventing the conductive layer 322 from peeling off or detaching from the elastic layer 321 during stretching. Thus, an electrical short circuit may be effectively prevented. In addition, the metal (e.g., metal cluster) present in the first depth region 321a of the elastic layer 321 may also serve as one electrical path, thereby maintaining stable electrical characteristics even during stretching.

The metal (e.g., metal cluster) and/or the conductive layer 322 present in the first depth region 321a of the elastic layer 321 may be electrically connected to the metal wire 310. For example, the metal (e.g., metal cluster) and/or a conductive layer 322 present in the first depth region 321a of the elastic layer 321 may be in contact with at least a portion of the metal wire 310. Therefore, even if a portion of the metal wire 310 is damaged or short-circuited, the electrical connection may be maintained by the metal (e.g., metal cluster) and/or the conductive layer 322 present in the first depth region 321a of the elastic layer 321, thereby maintaining stable electrical characteristics even during stretching.

The conductive elastic structure 320 may flexibly respond to external forces or external movements, such as twisting, pressing, and pulling in a particular (or, alternatively, predetermined) direction, and at the same time, as described above, by increasing adherence between the elastic layer 321 and the conductive layer 322 and maintaining the electrical connection with the metal wire 310, damage caused by external force or movement may be effectively reduced or prevented, and by stably securing an electrical path, ultimately, electrical stability according to stretching may be effectively increased.

The conductive elastic structure 320 may be formed by thermally depositing a metal on the aforementioned elastic layer 321 as described above. For example, the method of manufacturing the conductive elastic structure 320 may include preparing the elastic layer 321, and thermally depositing a metal on the elastic layer 321 to form the conductive layer 322.

The preparing of the elastic layer 321 may be obtained by, for example, applying an elastic polymer solution including an elastic polymer by a solution process such as spin coating, curing, and optionally patterning. The elastic polymer solution may further include, for example, a curing agent. As described above, the elastic polymer may be, for example, obtained by a copolymerization of a monomer or oligomer for at least one rigid structural unit and a monomer or oligomer for at least one soft structural unit at a particular (or, alternatively, predetermined) ratio so that a glass transition temperature of the copolymer may be less than or equal to about 80° C. For example, a weight ratio of the monomer or oligomer for the at least one soft structural unit to the monomer or oligomer for the at least one rigid structural unit may be less than about 1, and within the above range, less than or equal to about 0.9, less than or equal to about 0.8, less than or equal to about 0.7, less than or equal to about 0.6, less than or equal to about 0.5, less than or equal to about 0.4 or less, or less than or equal to about 0.3, about 0.01 to about 0.9, about 0.01 to about 0.8, about 0.01 to about 0.7, about 0.01 to about 0.6, about 0.01 to about 0.5, about 0.01 to about 0.4, or about 0.01 to about 0.3.

The forming of the conductive layer 322 may be performed by a method of forming a thin film at a temperature equal to or higher than the glass transition temperature of the elastic polymer, and may be, for example, performed by thermal deposition, vacuum, for example vacuum thermal deposition. For example, the forming of the conductive layer 322 may include preparing a thermal evaporator in which a boat or crucible including a metal sample and an elastic layer 321 face each other in a vacuum chamber, and applying heat to the boat or crucible to form the metal to evaporate the sample and to thermally deposit the metal on the surface of the elastic layer 321. The heat applied to the boat or crucible may be, for example, resistive heat.

For example, in the applying of the heat to the boat or crucible, the temperature inside the vacuum chamber may be increased by radiant heat generated by the heat, and the temperature of the vacuum chamber at this time may be, for example, equal to or higher than the glass transition temperature of the elastic polymer. In addition, in the applying of the heat to the boat or crucible, the surface temperature of the elastic layer 321 may also be increased by the radiant heat generated by the heat, and the surface temperature of the elastic layer 321 at this time may be, for example, equal to or higher than the glass transition temperature of the elastic polymer. As described above, as the surface temperature of the vacuum chamber and/or the elastic layer 321 increases, the flexibility and free space of the elastic polymer chains of the elastic layer 321 may be increased, and the penetration and/or diffusion of the metal into the elastic layer 321 may be increased.

The amount of metal that penetrates and/or diffuses into the elastic layer 321 may be controlled by, for example, a deposition rate. For example, in the case of deposition at a slow deposition rate for a long time, the depth (the first depth region 321a) at which metal atoms are diffused may be relatively deep. For example, in the case of deposition at a high deposition rate, the depth (the first depth region 321a) at which metal atoms are diffused may be relatively shallow. For example, the deposition rate of the metal may be for example greater than or equal to about 0.001 Å/s, greater than or equal to about 0.002 Å/s, greater than or equal to about 0.005 Å/s, greater than or equal to about 0.007 Å/s, greater than or equal to about 0.01 Å/s, greater than or equal to about 0.002 Å/s, greater than or equal to about 0.005 Å/s, or greater than or equal to about 0.007 Å/s, for example less than or equal to about 20 Å/s, within the above range, less than or equal to about 15 Å/s, less than or equal to about 10 Å/s, less than or equal to about 5 Å/s, less than or equal to about 3 Å/s, less than or equal to about 2 Å/s, less than or equal to about 1 Å/s, less than or equal to about 0.5 Å/s, less than or equal to about 0.4 Å/s, less than or equal to about 0.3 Å/s, less than or equal to about 0.2 Å/s, or less than or equal to about 0.1 Å/s, or within the above range, about 0.001 Å/s to about 20 Å/s, about 0.001 Å/s to about 15 Å/s, about 0.001 Å/s to about 10 Å/s, about 0.001 Å/s to about 5 Å/s, about 0.001 Å/s to about 3 Å/s, about 0.001 Å/s to about 2 Å/s, about 0.001 Å/s to about 1 Å/s, about 0.001 Å/s to about 0.5 Å/s, about 0.001 Å/s to about 0.4 Å/s, about 0.001 Å/s to about 0.3 Å/s, about 0.001 Å/s to about 0.2 Å/s, or about 0.001 Å/s to about 0.1 Å/s.

The metal atoms evaporated initially in the thermally depositing of the metal may easily penetrate and/or diffuse the surface of the elastic layer 321 having a relatively low glass transition temperature and may move into the elastic layer 321, and thus they may be distributed in an area up to a particular (or, alternatively, predetermined) depth from the surface of the elastic layer 321. Meanwhile, as the amount of metal atoms moved into the elastic layer 321 increases, at least a portion of the metal atoms may be aggregated with adjacent metal atoms and distributed in the form of metal clusters. When metal atoms and metal clusters are saturated at a particular (or, alternatively, predetermined) depth from the surface of the elastic layer 321, the penetration and/or diffusion of metal atoms into the interior stops and may be stacked on the surface of the elastic layer 321 so that the conductive layer 322 is formed.

As described above, the stretchable device 1000 according to some example embodiments includes the conductive elastic structure 320 formed locally in addition to the metal wire 310 in the connection wire 300 for connecting the active elements 200, so that it is possible to prevent damage and/or short circuit of the connection wire 300 by providing stretchability to the connection wire 300 in a portion where stress is concentrated during stretching and supplementing the electrical damage of the metal wire 310 due to stress concentration. Moreover, when the substrate 110 having a relatively high elastic modulus is used for mechanical stability of the active element 200, a geometrical deformation structure due to an incision line called a so-called "kirigami" structure in a region other than the region on which the active element 200 is disposed may be designed. As shown in at least FIGS. 1 and 3, the aforementioned conductive elastic structure 320 is disposed in a local area (e.g., a particular, limited portion) of the connection wire 300 where stress is concentrated by the geometrical deformation of the substrate 110 in such a "kirigami structure" to be connected to the connection wire 300 to provide the connection wire 300 with stretchability and to prevent damage and/or short circuit of the connection wire 300 by compensating for electrical damage to the metal wire 310 due to stress concentration. Accordingly, it is possible to ultimately increase the stretching stability of the stretchable device 1000.

The aforementioned stretchable device 1000 may be applied to (e.g., included in) various stretchable device systems requiring stretchability, for example, a display panel or a sensor. The stretchable device system may include, for example, a bendable display panel, a foldable display panel, a rollable display panel, a wearable device, and a skin-like display panel, a skin-like sensor, a large-area conformable display, smart clothing, etc., but the present inventive concepts are not limited thereto.

Figure 7:
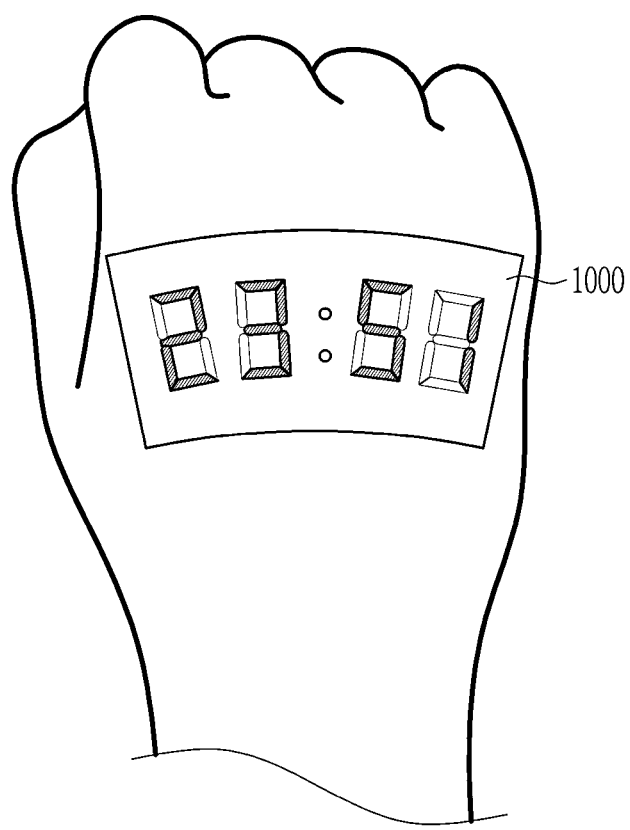
FIG. 7 is a schematic view showing a skin type display panel according to some example embodiments.
Figure 8A:
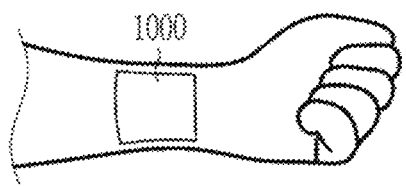
FIGS. 8A, 8B, and 8C are schematic views illustrating a sensor according to some example embodiments.
Figure 8B:
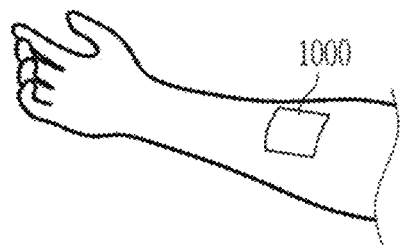
Figure 8C:
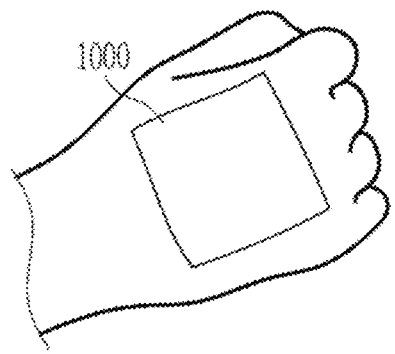

FIG. 7 is a schematic view illustrating a skin-type display panel according to some example embodiments, and FIGS. 8A, 8B, and 8C are schematic views illustrating a sensor according to some example embodiments.

Referring to FIG. 7, the aforementioned stretchable device 1000 may be and/or may be included in a skin-type display panel that is an ultrathin display panel, and may display particular (or, alternatively, predetermined) information such as various characters and/or images.

Referring to FIGS. 8A to 8C, the aforementioned stretchable device 1000 may be and/or may be included in an attachable biological sensor, and may be attached to a surface of a living body such as a skin, a living body such as an organ, or an indirect means for contacting a living body such as clothing to detect and measure biological information such as a biological signal. For example, the biological sensor includes an electroencephalogram (EGG) sensor, an electrocardiogram (ECG) sensor, a blood pressure (BP) sensor, an electromyography (EMG) sensor, a blood glucose (BG) sensor, a photoplethysmography (PPG) sensor, an accelerometer, a RFID antenna, an inertial sensor, an activity sensor, a strain sensor, a motion sensor, or a combination of these, but is not limited thereto. The biological sensor may be attached to a living body in a very thin patch-type or band-shaped form, so that the biological information may be monitored in real time.

As an example, the stretchable device 1000 may be a photoplethysmography sensor (PPG sensor), and the biological information may include a heart rate, oxygen saturation, stress, arrhythmia, blood pressure, and the like, and may be obtained by analyzing waveforms of electric signals.

For example, the stretchable device 1000 may be an electromyography (EMG) sensor or a strain sensor attached to a joint for rehabilitation treatment of patients with joint and muscle problems. The electromyography (EMG) sensor or the strain sensor may be attached to a desired site to quantitatively measure muscle movement or joint movement to secure data necessary for rehabilitation.

The aforementioned stretchable device; or the stretchable device system such as a display panel and a sensor may be included in various electronic devices, and the electronic device may further include a processor (not shown) and a memory (not shown). The electronic device may be a mobile; TV; a health care device, and the like, and the health care device may be, for example, a photoplethysmography (PPG) sensor, an electroencephalogram (EEG) sensor, an electrocardiogram (ECG) sensor, a blood pressure (BP) sensor, an electromyography (EMG) sensor, a blood glucose (BG) sensor, an accelerometer device, a RFID antenna device, an inertial sensor, an activity sensor, a strain sensor, a motion sensor, or any combination thereof, but is not limited thereto.

Any of the devices, systems, elements, units, packages, or the like as described herein (e.g., any of the electronic devices, display panels, sensors, device systems, or the like including the stretchable device 1000 according to any of the example embodiments) may be included in, include, and/or implement one or more instances of processing circuitry such as hardware including logic circuits, a hardware/software combination such as a processor executing software; or any combination thereof. In some example embodiments, said one or more instances of processing circuitry may include, but are not limited to, a central processing unit (CPU), an application processor (AP), an arithmetic logic unit (ALU), a graphic processing unit (GPU), a digital signal processor, a microcomputer, a field programmable gate array (FPGA), a System-on-Chip (SoC) a programmable logic unit, a microprocessor, or an application-specific integrated circuit (ASIC), etc. In some example embodiments, any of the memories as described herein may include a non-transitory computer readable storage device, for example a solid state drive (SSD), storing a program of instructions, and the one or more instances of processing circuitry may be configured to execute the program of instructions to implement the functionality of some or all of the devices, systems, elements, units, packages, or the like as described herein, or the like according to any of the example embodiments as described herein.

While the inventive concepts have been described in connection with what is presently considered to be practical example embodiments, it is to be understood that the inventive concepts are not limited to such example embodiments. On the contrary, the inventive concepts are intended to cover various modifications and equivalent arrangements included within the spirit and scope of the appended claims.

What is claimed is:

1. A stretchable device, comprising:
    a stretchable substrate, the stretchable substrate having a plurality of incision lines that are configured to be deformable by an external force applied to the stretchable substrate,
    a plurality of active elements on the stretchable substrate, and
    a connection wire configured to electrically connect adjacent active elements of the plurality of active elements,
    wherein the connection wire includes
        a metal wire, and
        a conductive elastic structure electrically connected to the metal wire, the conductive elastic structure being in a particular, limited portion of the connection wire.

2. The stretchable device of claim 1, wherein
    the stretchable substrate comprises
        a plurality of island-shaped regions, the plurality of active elements being on separate, respective island-shaped regions of the plurality of island-shaped regions, and
        a stretchable region excluding the plurality of island-shaped regions, and the plurality of incision lines are in the stretchable region.

3. The stretchable device of claim 2, wherein the connection wire is on the stretchable region of the stretchable substrate.

4. The stretchable device of claim 1, wherein the conductive elastic structure is in contact with a portion of the metal wire that is configured concentrate stress in the metal wire based on deformation of at least the stretchable substrate.

5. The stretchable device of claim 1, wherein the conductive elastic structure is in contact with an edge portion of the metal wire, a center portion of the metal wire, or any combination thereof.

6. The stretchable device of claim 1, wherein the conductive elastic structure is on a particular portion of the metal wire, or at least a portion of the conductive elastic structure is embedded in the metal wire.

7. The stretchable device of claim 1, wherein the conductive elastic structure comprises a combination of
    an elastic polymer, and
    at least one of a metal, a liquid metal, or a conductive nanostructure.

8. The stretchable device of claim 7, wherein
    the conductive elastic structure comprises
        an elastic layer comprising the elastic polymer, and
        a conductive layer on the elastic layer, the conductive layer comprising the metal,
    the elastic layer comprises a first depth region and a second depth region sequentially disposed in a depth direction from a surface that is in contact with the conductive layer, and
    the first depth region includes the metal.

9. The stretchable device of claim 8, wherein
    the elastic polymer is a copolymer comprising at least one rigid structural unit and at least one soft structural unit, and
    a weight ratio of the rigid structural unit to the soft structural unit is greater than about 0.01 and less than about 1.

10. The stretchable device of claim 9, wherein
    the rigid structural unit comprises a styrene structural unit, an olefin structural unit, a urethane structural unit, an ether structural unit, or any combination thereof, and
    the soft structural unit comprises an ethylene structural unit, a propylene structural unit, a butylene structural unit, an isobutylene structural unit, a butadiene structural unit, an isoprene structural unit, or any combination thereof.

11. The stretchable device of claim 8, wherein the metal comprises gold (Au), silver (Ag), copper (Cu), rhodium (Rh), palladium (Pd), ruthenium (Ru), osmium (Os), iridium (Ir), platinum (Pt), an alloy thereof, or any combination thereof.

12. The stretchable device of claim 8, wherein the metal in the first depth region of the elastic layer exists in a form of a metal cluster.

13. The stretchable device of claim 12, wherein the conductive layer is electrically connected to the metal cluster of the elastic layer.

14. The stretchable device of claim 12, wherein the metal cluster or the conductive layer of the elastic layer is electrically connected to the metal wire.

15. The stretchable device of claim 8, wherein the conductive layer comprises a plurality of microcracks.

16. The stretchable device of claim 1, wherein each active element of the plurality of active elements comprises a transistor, a light emitting element, a light absorption element, a resistive element, an imaging element, or any combination thereof.

17. A display panel comprising the stretchable device of claim 1.

18. A sensor comprising the stretchable device of claim 1.

19. An electronic device comprising the display panel of claim 17.

20. An electronic device comprising the sensor of claim 18.

* * * * *